United States Patent [19]

Koga et al.

[11] 4,292,433

[45] Sep. 29, 1981

[54] METHOD FOR PRODUCING 3-CHLOROPROPYLTRICHLOROSILANE

[75] Inventors: Isao Koga, Sakurashi; Yohji Terui, Chibashi; Masuhito Ohgushi, Minamatashi; Tohru Kitahara, Minamatashi; Kenichi Watanabe, Minamatashi, all of Japan

[73] Assignee: Chisso Corporation, Osaka, Japan

[21] Appl. No.: 202,621

[22] Filed: Oct. 31, 1980

[51] Int. Cl.³ ............................................... C07F 7/08
[52] U.S. Cl. .................................. 556/479; 252/431 P
[58] Field of Search ......................................... 556/479

[56] References Cited

U.S. PATENT DOCUMENTS 4,242,272 12/1980 Koga et al. ........................ 556/489

FOREIGN PATENT DOCUMENTS 44-18844 8/1969 Japan.
51-95023 8/1976 Japan.

OTHER PUBLICATIONS

Ryan et al., "J.A.C.S.", 82, p. 3601, 1960.

Primary Examiner—Paul F. Shaver
Attorney, Agent, or Firm—Fred Philpitt

[57] ABSTRACT

In the method of producing 3-chloropropyltrichlorosilane by the addition reaction of trichlorosilane to allyl chloride, [Pt(PPh$_3$)$_2$Cl$_2$] is used as the catalyst for the reaction.

Side reactions are suppressed to give a high yield of the product.

2 Claims, No Drawings

METHOD FOR PRODUCING 3-CHLOROPROPYLTRICHLOROSILANE

BACKGROUND OF THE INVENTION

This invention relates to a production method of 3-chloropropyltrichlorosilane.

The addition reaction of trichlorosilane to allyl chloride is disclosed in the report of J. W. Ryan [J. Am. Chem. Soc. 82, 3601 (1960)] and Japanese patent application laid-open No. 95,023/1976, but this reaction is accompanied with many side reactions, resulting in poor yield of 3-chloropropyltrichlorosilane. Further, Japanese patent publication No. 18,844/1969 discloses a method by way of a γ-ray irradiation of Co-60, but the method is commercially disadvantageous and poor in practical value because the reaction apparatus used in the method is complicated and the initial cost is high.

SUMMARY OF THE INVENTION

The object of the present invention is to provide a method for producing 3-chloropropyltrichlorosilane in which the above-mentioned disadvantages of the prior art have been overcome, and 3-chloropropyltrichlorosilane is produced with a higher yield.

The production method of the present invention is characterized in carrying out the addition reaction of trichlorosilane to allyl chloride into 3-chloropropyltrichlorosilane, in the presence of dichloro-bis(triphenylphosphine) platinum (II) [Pt(PPh$_3$)$_2$Cl$_2$].

DESCRIPTION OF PREFERRED EMBODIMENTS

According to the present invention, trichlorosilane is mixed with allyl chloride; dichloro-bis(triphenylphosphine) platinum (II) as a catalyst is added to the mixture; and reaction is carried out by heating the mixture at a temperature of 30° to 160° C. to produce 3-chloropropyltrichlorosilane. The mixing ratio by mol of trichlorosilane to allyl chloride is in the range of 1:1 to 4:1, preferably 1:1 to 2:1. The amount of Pt(PPh$_3$)$_2$Cl$_2$ used is in the range of 0.01 to 0.5 % by mol, preferably 0.02 to 0.1 % by mol based upon one mol of trichlorosilane. The reaction temperature is in the range of 30° to 160° C., preferably 60° to 120° C. The reaction time is in the range of 1 to 10 hours. The reaction is carried out either under reflux under the atmospheric pressure or at a high temperature under pressure, but it is preferable to carry out the reaction under pressure. If necessary, a solvent such as chlorobenzene, xylene, toluene or the like may be used in the reaction.

The apparatus used in the production method of the present invention may be any one of batchwise type, continuous type, etc.

The characteristic feature of the present invention is that 3-chloropropyltrichlorosilane is obtained with a high yield by using dichloro-bis[triphenylphosphine] platinum (II) [Pt(PPh$_3$)$_2$Cl$_2$] as the catalyst for the reaction.

In the reaction expressed by the following equation (1), chloroplatinic acid has heretofore been used as the catalyst for the reaction, but a side reaction expressed by the following equation (2) occurs, resulting in a notable reduction in the yield:

$$ClCH_2CH=CH_2 + HSiCl_3 \rightarrow ClCH_2CH_2CH_2SiCl_3 \quad (1)$$

$$ClCH_2CH=CH_2 + HSiCl_3 \rightarrow CH_3CH=CH_2 + SiCl_4 \quad (2)$$

The catalyst of the present invention is characterized in that side reactions such as equation (2) are notably suppressed. As a result, the amount of byproducts is notably reduced to give a high yield of 3-chloropropyltrichlorosilane. On the other hand, platinum complexes other than the catalyst of the present invention, e.g. tetrakistriphenyl phosphine platinum (0), are entirely ineffective.

The following examples are given to illustrate the present invention but it is not intended to limit the scope of the invention.

EXAMPLE 1

Twenty three grams (0.17 mol) of trichlorosilane, 7.7 g (0.1 mol) of allyl chloride and 0.05 % by mol (based upon one mol of trichlorosilane) of a catalyst Pt(PPh$_3$)$_2$Cl$_2$ were introduced into a 100 ml stainless steel pressure reactor. After sealing, reaction was carried out with stirring at a temperature of 100° C. for 8 hours. After completion of the reaction, the reaction liquid was analysed. The results are shown in the Table mentioned below. The reaction yield of 3-chloropropyltrichlorosilane based upon the amount of allyl chloride was 82%.

EXAMPLE 2

Example 1 was repeated except that 20.3 g (0.15 mol) of trichlorosilane, 7.7 g (0.1 mol) of allyl chloride and 0.025 mol % of the catalyst were used. The results are shown in the Table.

COMPARATIVE EXAMPLE 1

Example 1 was repeated except that H$_2$PtCl$_6$.6H$_2$O was used in place of the catalyst of Example 1. The results are shown in the Table.

COMPARATIVE EXAMPLE 2

Example 1 was repeated except that Pt(PPh$_3$)$_4$ was used in place of the catalyst of Example 1. The results are shown in the Table.

TABLE

| Product | | Examples 1 | Examples 2 | Comparative examples 1 | Comparative examples 2 |
|---|---|---|---|---|---|
| Composition | Cl(CH$_2$)$_3$SiCl$_3$ | 63.7 | 69.8 | 33.6 | 33.3 |
| of | H$_3$C(CH$_2$)$_2$SiCl$_3$ | 11.7 | 11.1 | 31.8 | 12.7 |
| reaction | SiCl$_4$ | 11.2 | 10.6 | 28.6 | 31.5 |
| liquid (%) | H$_2$C=CHCH$_2$SiCl$_3$ | 0 | 0 | 0 | 22.5 |
|  | HSiCl$_3$ | 13.4 | 8.5 | 0 | 0 |
| Reaction yield* (%) | | 82.0 | 83.9 | 46.9 | 44 |

*Yield of 3-chloropropyltrichlorosilane based on allyl chloride

What is claimed is:

1. In the method for producing 3-chloropropyltrichlorosilane by the addition reaction of trichlorosilane to allyl chloride, the improvement comprising reacting said reactants in the presence of a complex of dichloro-bis(triphenylphosphine) platinum (II), [Pt(PPh$_3$)$_2$Cl$_2$].

2. A method according to claim 1 wherein the reaction temperature is in the range of 30° to 160° C. and the amount of said complex used is in the range of 0.01 to 0.5% by mol based upon one mol of trichlorosilane.

* * * * *